(12) United States Patent
Bessant et al.

(10) Patent No.: US 11,644,365 B2
(45) Date of Patent: May 9, 2023

(54) AEROSOL-GENERATING DEVICE AND SYSTEM COMPRISING A PYROMETER

(71) Applicant: PHILIP MORRIS PRODUCTS S.A., Neuchatel (CH)

(72) Inventors: Michel Bessant, Neuchatel (CH); Jacques Robert, Le Mont-sur-Lausanne (CH); Riccardo Riva Reggiori, St. Sulpice (IT); Alexandru Rusu, Lausanne (CH); Peter Seitz, Urdorf (CH)

(73) Assignee: Philip Morris Products S.A., Neuchatel (CH)

( * ) Notice: Subject to any disclaimer, the term of this patent is extended or adjusted under 35 U.S.C. 154(b) by 377 days.

(21) Appl. No.: 16/650,914

(22) PCT Filed: Oct. 2, 2018

(86) PCT No.: PCT/EP2018/076702
§ 371 (c)(1),
(2) Date: Mar. 26, 2020

(87) PCT Pub. No.: WO2019/068664
PCT Pub. Date: Apr. 11, 2019

(65) Prior Publication Data
US 2020/0269267 A1    Aug. 27, 2020

(30) Foreign Application Priority Data

Oct. 3, 2017   (EP) .................................... 17194566

(51) Int. Cl.
*G01J 5/60*  (2006.01)
*A24F 42/10*  (2020.01)
(Continued)

(52) U.S. Cl.
CPC ............... *G01J 5/60* (2013.01); *A24F 40/51* (2020.01); *A24F 42/10* (2020.01); *B05B 12/004* (2013.01);
(Continued)

(58) Field of Classification Search
CPC .... G01J 5/60; G01J 5/06; G01J 5/0802; G01J 5/602; G01J 2005/065; G01J 3/42;
(Continued)

(56) References Cited

U.S. PATENT DOCUMENTS 3,896,313 A   7/1975  Berman
5,326,172 A   7/1994  Ng
(Continued)

FOREIGN PATENT DOCUMENTS

CN    104305527    1/2015
DE    202014101125    6/2014
(Continued)

OTHER PUBLICATIONS

Gardner, J. L., "Effective wavelength for multicolor/pyrometry", *Applied Optics*, vol. 19, No. 18, Sep. 15, 1980 (4 pages).
(Continued)

*Primary Examiner* — David P Porta
*Assistant Examiner* — Gisselle M Gutierrez
(74) *Attorney, Agent, or Firm* — Mueting Raasch Group (57) ABSTRACT

The present invention relates to an aerosol-generating device that is configured for generating an inhalable aerosol by heating an aerosol-forming substrate. The device comprises a device housing for receiving the aerosol-forming substrate and a pyrometer for determining a temperature of a heated target surface within the device housing. The invention further relates to an aerosol-generating system comprising
(Continued)

such an aerosol-generating device and an aerosol-generating article for use with the device including an aerosol-forming substrate.

11 Claims, 2 Drawing Sheets

(51) Int. Cl.
    *A24F 40/51*        (2020.01)
    *B05B 12/00*        (2018.01)
    *B05B 12/10*        (2006.01)
    *G01J 5/06*         (2022.01)
    *G01J 5/0802*      (2022.01)
    *A24F 40/10*        (2020.01)
    *A24F 40/20*        (2020.01)

(52) U.S. Cl.
    CPC .............. *B05B 12/10* (2013.01); *G01J 5/06* (2013.01); *G01J 5/0802* (2022.01); *G01J 5/602* (2013.01); *A24F 40/10* (2020.01); *A24F 40/20* (2020.01); *G01J 2005/065* (2013.01)

(58) Field of Classification Search
    CPC ............ G01J 2005/0074; G01J 5/0066; G01J 5/0806; G01J 5/0878; G01J 5/08; A24F 40/51; A24F 42/10; A24F 40/10; A24F 40/20; A24F 40/465; B05B 12/004; B05B 12/10; A61M 11/402; A61M 2205/3306; A61M 2205/3368; A61M 2205/3653; A61M 2205/368; A61M 15/06
    See application file for complete search history.

(56) References Cited

U.S. PATENT DOCUMENTS

| | | | |
|---|---|---|---|
| 8,309,924 B2 | 11/2012 | Burghartz | |
| 10,189,632 B2* | 1/2019 | Bessant | B65D 83/384 |
| 11,091,314 B2* | 8/2021 | Bessant | H05B 1/0244 |
| 2003/0033110 A1* | 2/2003 | Schietinger | G01J 5/08 |
| | | | 374/E11.003 |
| 2005/0016550 A1 | 1/2005 | Katase | |
| 2007/0045288 A1 | 3/2007 | Nelson | |
| 2007/0177650 A1* | 8/2007 | Huston | G01J 5/0802 |
| | | | 374/130 |
| 2010/0278212 A1 | 11/2010 | Burghartz | |
| 2012/0183013 A1 | 7/2012 | Stein | |
| 2016/0021930 A1 | 1/2016 | Minskoff | |
| 2016/0262451 A1 | 9/2016 | Liu | |
| 2016/0271347 A1 | 9/2016 | Raichman | |
| 2017/0265524 A1 | 9/2017 | Cadieux | |
| 2018/0072487 A1* | 3/2018 | Bessant | B65D 83/752 |
| 2018/0143004 A1* | 5/2018 | Bonin | G01J 5/602 |
| 2019/0152685 A1* | 5/2019 | Bessant | B65D 83/384 |

FOREIGN PATENT DOCUMENTS

| | | |
|---|---|---|
| JP | 2008-60464 | 3/2008 |
| JP | 2008-060464 | 3/2008 |
| JP | 2011-503560 | 1/2011 |
| RU | 83387 | 6/2009 |
| WO | WO 2010/111780 | 10/2010 |
| WO | WO 2010/115143 | 10/2010 |
| WO | WO 2014/115143 | 7/2014 |
| WO | WO 2016/184783 | 11/2016 |
| WO | 2017/162687 | 9/2017 |

OTHER PUBLICATIONS

Dual Sandwich Detector Series—OSI Opotoelectronics (6 pages).
International Preliminary Examination Report on Patentability for PCT/EP2018/076702, dated Jan. 9, 2020 (11 pages).
International Search Report and Written Opinion for PCT/EP2018/076702 dated Nov. 27, 2018 (11 pages).
Office Action issued in Russia for Application No. 2020115093 dated Nov. 29, 2021 (4 pages). English translation included.
Office Action issued in Japan for Application No. 2020-518816 dated Sep. 6, 2022 (9 pages). English translation included.

* cited by examiner

AEROSOL-GENERATING DEVICE AND SYSTEM COMPRISING A PYROMETER

This application is a U.S. National Stage Application of International Application No. PCT/EP2018/076702 filed Oct. 2, 2018, which was published in English on Apr. 11, 2019 as International Publication No. WO 2019/068664 A1. International Application No. PCT/EP2018/076702 claims priority to European Application No. 17194566.0 filed Oct. 3, 2017.

The present invention relates to an aerosol-generating device for generating an inhalable aerosol by heating an aerosol-forming substrate. The invention further relates to an aerosol-generating system comprising such a device.

Aerosol-generating devices for generating an inhalable aerosol by heating an aerosol-forming substrate are generally known from prior art. Within such devices, the aerosol-forming substrate is heated either chemically, for example by thermal energy generated by an exothermal chemical reaction, or electrically, for example by a resistive or inductive heater. Accurate temperature control of the heating process is crucial because the aerosol-forming substrate is intended to be heated only rather than combusted in order to ensure that only desired aerosol-forming volatile compounds are released. Accurate temperature control in turn relies on accurate temperature monitoring. For resistive devices, the heating temperature can be determined over a sufficient range from a known relationship between temperature and resistivity of the heating element. Yet, for inductive devices, only a temperature threshold can be determined, for example when the magnetic properties of a susceptive heating material change from ferromagnetic to paramagnetic at the Curie temperature of the heating material. Likewise, thermocouples or other temperature sensors are used for temperature monitoring. Typically, such sensors required thermal contact with the object to be measured, for example with a heating element arranged within the aerosol-forming substrate. However, thermal contact measurements are prone to failure, for example, when the temperature sensor breaks off, or when the temperature sensor does not make proper thermal contact with the heating element upon being inserted together with the substrate into the aerosol-generating device.

Therefore, it would be desirable to have an aerosol-generating device and an aerosol-generating system allowing for a reliable, fast and reproducible temperature monitoring of the heating process used for aerosol formation.

According to the invention there is provided an aerosol-generating device that is configured for generating an aerosol by heating an aerosol-forming substrate. The device comprises a device housing for receiving the aerosol-forming substrate to be heated. According to the invention, the device further comprises a pyrometer for determining a temperature of a heated target surface within the device housing.

Using a pyrometer for temperature monitoring within an aerosol-generating device proves advantageous with regard to many aspects. First, pyrometers allow for remote non-contact temperature measurements. Thus, pyrometers provide highly reliable and reproducible results as dysfunctions due to improper or broken thermal contacts are avoided. Second, due to the capability of remote measurements, the pyrometer does not interfere with the heated target surface. Thus, there is no undesired temperature effect on the target surface due to heat conduction from the target surface to the pyrometer. This also makes the measurement highly reliable. At the same time, undesired heat transfer to other components of the aerosol-generating device, for example, to an electric circuitry, is reduced. Third, the capability of contactless temperature measurement facilitates replacement of the heated target surface. For example, the target surface may be a surface area of a heating element being part of an aerosol-generating article which includes the aerosol-forming substrate to be heated by the heating element. Fourth, pyrometers allow for fast temperature measurements in the millisecond range and thus for a continuous temperature monitoring of the target surface. Fifth, pyrometers are capable of measuring high temperatures, at least those temperatures which are typical for aerosol formation of tobacco containing aerosol-forming substrates. Sixth, the pyrometer has no mechanical effect on the target surface due to the contactless nature of the temperature measurement. Thus, also soft or fragile target surfaces, for example susceptor foils or susceptor meshes can be measured without the risk of mechanical damages. Seventh, due to the optical nature of the measurement, it is possible to make local spot-measurements of the temperature on the target surface with a lateral resolution down to the micrometer range. Likewise, a two-dimensional temperature distribution can be measured with the aid of an imaging pyrometer.

Preferably, the pyrometer is configured for monitoring temperatures between 150 degree Celsius and 400 degree Celsius, in particular between 200 degree Celsius and 350 degree Celsius. These temperatures are typical operation temperatures of aerosol-generating devices.

In pyrometers, Planck's law or Wien's approximation are used to infer the temperature of the target surface from the measured spectral thermal radiance of the target surface taking into account the emissivity of the heated target surface, that is, the effectiveness of the target surface in emitting energy as thermal radiation. To determine the temperature from the measured radiance, the emissivity of the heated target surface has to be known or determined. In principle, emissivity can be measured using an apparatus which, for example, comprises a Leslie's cube in conjunction with a thermal radiation detector, such as a thermopile or a bolometer. The apparatus compares the thermal radiation from the target surface to be tested with the thermal radiation from a nearly ideal, black sample.

In case the pyrometer is to be used for monitoring only a small range of typical operation temperatures, for example, a range having a width of some ten Kelvin, the emissivity of the target surface can be considered to be constant within this range. Accordingly, the emissivity of the target surface can be determined once for this temperature range in a separate measurement and consequently used for calibration of the pyrometer.

For measuring thermal radiation emitted by the heated target surface the pyrometer may comprise a detector for converting the received thermal radiation into an electrical output signal. Advantageously, the detector comprises a spectral sensitivity range corresponding to the thermal radiation spectrum of the target surface at a specific temperature or temperature range of interest.

Preferably, the detector may be a photodetector (sometimes also called quantum detector). Photodetectors or quantum detectors interact directly with the impacting photons of the thermal radiation, resulting in electron pairs and thus in an electrical output signal. Preferably, the photodetector may be or may comprise one or more photodiodes. For example, the one or more photodiodes may comprise a photosensitive material select from at least one of: Si (silicon), Ge (germanium), InGaAs (indium gallium arsenide), InAs (indium arsenide), InSb (indium antimonide), InAsSb (indium arsenid antimonide), or PbS (lead(II) sulfide. The spectral sensitivity ranges of these materials prove advantageous with regard to the spectrum of thermal radiation which is typically emitted at temperatures between 200 degree Celsius and 350 degree Celsius by a heating element used in an aerosol-generating device. The spectral sensitivity ranges of the above materials are as follows: Si is sensitive for wavelengths between 0.2 micrometer and 1.1 micrometer, Ge is sensitive for wavelengths between 0.4 micrometer and 1.7 micrometer, InGaAs is sensitive for wavelengths between 0.9 micrometer and 1.7 micrometer, InAs is sensitive for wavelengths between 0.9 micrometer and 3.5 micrometer, InSb is sensitive for wavelengths between 1.2 micrometer and 7 micrometer, InAsSb is sensitive for wavelengths between 1.0 and 5.5 microns, and PbS is sensitive for wavelengths between 0.3 micrometer and 3 micrometer. The respective upper edge of these ranges, that is, the long-wave end of the spectral sensitivity range is basically determined by the band gap energy of the respective semiconductor material.

InGaAs photodiodes are preferred as having a faster response time, higher quantum efficiency and lower dark current for the same sensor area as compared to other materials, such as Ge.

Instead of photodiodes, the photodetector may comprise at least one photoresistor, for example, comprising PbS (lead(II) sulfide).

Alternatively, the detector may be a thermal detector, for example a bolometer, a pyroelectric infrared sensor or a thermopile composed of a plurality of thermocouples. Thermal detectors experience a temperature change depending on the impacting thermal ration which in turn creates an electrical output voltage.

The pyrometer may comprise an optical system for collecting thermal radiation emitted from the heated target surface and for directing the thermal radiation towards the detector. In particular, the optical system may comprise at least one lens or a lens system, for transferring thermal radiation from the target surface to the detector of the pyrometer. The optical system preferably has a lateral resolution (on the target surface) of 1 millimeter or below, in particular of 100 micrometer or below, preferably of 10 micrometer or below, most preferably of 5 micrometer and below, for example of about 3 micrometer or about 2 micrometer.

The optical system preferably may have a full field of view (diameter of the object on the target surface) having a diameter of at least 0.1 millimeter, in particular of at least 1 millimeter, preferably of at least 3 millimeter, most preferably of at least 5 millimeter. That is, the optical system preferably is configured to collect thermal radiation emitted from an area of the heated target surface, the area having a diameter of at least 0.1 millimeter, in particular of at least 1 millimeter, preferably of at least 3 millimeter, most preferably of at least 5 millimeter.

The pyrometer may also comprise means for restricting the spectral band of the thermal radiation sensed by the detector. Accordingly, the pyrometer may comprise at least one filter. In particular, the at least one filter may be an optical bandpass or an optical longpass filter or an optical shortpass filter: The pyrometer may also comprise a combination of such filters. The at least one filter may be an interference filter, an absorption filter or a diffractive optical filter. In particular, the filter may be an intrinsic filter of the detector. Further details of specific filter configurations are discussed below.

The pyrometer may further comprise an electrical circuitry for converting the output signal of the detector into a signal indicative of the temperature of the target surface. Likewise, the electrical circuitry may be part of a controller of the overall aerosol-generating device used to control the heating process of the device. In particular, the pyrometer, that is, the temperature determined by the pyrometer, may be used for feedback control of the heating process of the device.

The electrical circuitry may comprise at least one of a transimpedance amplifier for current-to-voltage conversion, an inverting signal amplifier, a single-ended to-differential converter, an analog-digital converter and a micro-controller.

In principle, the pyrometer according to the invention may be a single-wavelength pyrometer, a dual-wavelength pyrometer or a multiple-wavelength pyrometer.

In case of a single-wavelength pyrometer, the pyrometer is configured for detecting the thermal radiation emitted by the heated target surface at a single wavelength band. A single-wavelength pyrometer proves advantageous due to its simple and low-cost design. For example, a single-wavelength pyrometer may comprise a single photodetector having a single photodiode and a single-element optical system, for example a single collecting lens arranged in front of the photodiode. Furthermore, the single-wavelength pyrometer may comprise a filter, in particular a bandpass filter in front of the detector in order to restrict the spectral band of radiation sensed by the detector. Advantageously, filtering reduces undesired effects due to spectral variation of the emissivity, which has to be necessarily known or determined when using a single-wavelength pyrometer. As described above, single-wavelength pyrometers are particularly suitable for monitoring target surfaces of known emissivity over a small range of operation temperatures.

Alternatively, the pyrometer may be a dual-wavelength pyrometer. Dual-wavelength pyrometers detect thermal radiation emitted by a target surface at two wavelength bands. The ratio of the two spectral radiances varies monotonically (in fact, almost proportionally) to the temperature and can thus be converted into an accurate temperature value. Accordingly, when using a dual-wavelength pyrometer, the temperature measurement is dependent only on the ratio of the two measured radiances, but not on their absolute values. More precisely, the temperature of the target surface is a function of both, the ratio of the two radiances measured at the two wavelength bands and the ratio of the respective emissivities at the two wavelength bands. For this reason, dual-wavelength pyrometers are also called ratio pyrometers. Furthermore, any parameter, such as the ratio between the size of the target surface and the field of view (FOV) of the detector, which affects the absolute value of the radiance at the two wavelengths or wavelength bands by an equal percentage, has no effect on the temperature measurement. Therefore, using a dual-wavelength pyrometer makes the temperature measurement independent of the size of the target surface. Likewise, changing transmittance characteristics in the measurement path between the target surface and the detector are eliminated in the same way due to the measured temperature being dependent only on the ratio of the two measured radiances. This proves particularly advantageous with regard to temperature monitoring within an aerosol-generating device where the generated aerosol or dust in the line-of-sight of the pyrometer may reduce the absolute value of the thermal radiance sensed by the detector. Furthermore, when the emissivities at the two wavelength bands are substantially equal, the ratio of the respective emissivities at the two wavelength bands is about unity. Consequently, emissivity is factored out in the temperature function used to calculate the temperature of the target surface. Accordingly, the dual-wavelength pyrometer shows the true temperature of the target surface no matter what the actual value of the emissivity of the target surface is.

In general, the dual wavelength pyrometer may be configured to measure thermal radiation at least at two wavelength bands that are separate and distinct from each other. That is, the first wavelength band and the second wavelength band may be separate and distinct from each other. This configuration corresponds to a dual wavelength pyrometer in its classical meaning. Alternatively, the dual wavelength pyrometer may be configured to measure thermal radiation at least at two wavelength bands that partially overlap which each other or wherein one of the two wavelength bands is a subset of the other wavelength band. This configuration corresponds to a dual wavelength pyrometer which sometimes is also called a two-color pyrometer. That is, the first wavelength band and the second wavelength band may partially overlap which each other or the first wavelength band may be a subset of the second wavelength band.

In order to have the emissivities at the two wavelength bands being substantially equal or in order to at least minimize wavelength-dependent deviations of the emissivity, the two wavelength bands are preferably chosen to be close together, and preferably also narrow-banded (assumption of grey body behavior). Even when the emissivity of the target object varies to the same extent at both wavelength bands, the measurement result will not be changed. Deviations from the true temperature as a result of constant differences or linear relationship between the two emissivities can be corrected by setting an emissivity ratio on the pyrometer (so called e-slope).

Increasing the separation between the two wavelength bands may be used to reduce the temperature measurement uncertainty. However, with increasing separation, the assumption on the grey body behavior of the target surface may become less valid. Therefore, the choice of the two wavelength bands should be a compromise between grey body behavior and temperature measurement uncertainty.

In conclusion, dual-wavelength pyrometers are inherently accurate as they allow for compensating for emissivity variations, partially filled fields of view and optical obstructions between the target surface and the detector of the pyrometer.

The two wavelength bands may have the same bandwidth or different bandwidths. That is, instead of measuring at two narrow wavelength bands, the dual-wavelength pyrometer may be configured to measure thermal radiation at a first wavelength band and at second wavelength band wherein the second wavelength band is broader than the first wavelength band. In doing so, the difference between the respective thermal radiances measured at these wavelength bands increases, which advantageously improves the signal level to be measured. Otherwise, when the two wavelength bands are close together, the respective thermal radiances measured at these wavelength bands hardly differ from each other. Thus, the ratio of the two nearly identical radiance values varies only slightly in relation to the temperature of the target surface. Therefore, the electric circuitry preferably is configured to provide a large amplification factor in order to detect such small signal changes.

In case of measuring not at a singular wavelength or not at a narrow wavelength band, the detector measures an integrated radiance over the wavelength band. Yet, most formulae used to derive a temperature of the target surface refer to the spectral thermal radiation at a specific wavelength or within a narrow wavelength band. To still derive a temperature, the integrated radiance may be obtained by calculation of the radiance at a so-called effective wavelength which represents the mean radiance at a given radiance, weighted by the spectral response of the detector and possible filters in front of the detector. As regards the determination of the effective wavelength, further reference is made, for example, to the article "Effective wavelength for multicolor/pyrometry" by J. L. Gardner, Applied Optics, Vol. 19, Issue 18, pp. 3088-3091 (1980).

As an alternative to determining an effective wavelength, the pyrometer may be calibrated over the wavelength band or even over the full wavelength spectrum. By this, possible variations in the transmissivity of the optical system or in the transmissivity of an entrance window of the pyrometer are advantageously taken into account automatically. Calibration can be done for example by using a blackbody emitter at different known temperatures of the blackbody. Once the pyrometer is calibrated, the emissivity of the heated target surface is not needed to be known anymore.

For detecting radiation at a respective first and second wavelength band, the pyrometer may comprise a detector including at least a first and a second sensor. The first and second sensors are arranged and configured such as to independently detect a respective portion of the thermal radiance emitted by the target surface. For example, the photodetector may comprise at least a first and a second photodiode which are independent of each other. Likewise, the photodetector may comprise a single photodiode having at least a first and a second sensor area (acting as first and second sensor) for independently measuring a respective portion of the emitted thermal radiance. The first and the second sensor may be arranged adjacent to each other side by side, in particular in a single detection plane. Alternatively, the first and the second sensor may be arranged one in front of the other in a sandwich configuration. In the latter configuration, the respective front sensor may advantageously represent a filter for the respective back sensor.

For selecting two respective wavelength bands, the dual-wavelength pyrometer may comprise a first bandpass or longpass or shortpass filter. Additionally or alternatively, the dual-wavelength pyrometer may comprise a second bandpass or longpass or shortpass filter.

As regards the use of bandpass filters, the bandwidth preferably corresponds to the first or second wavelength/wavelength band, respectively. A bandwidth of the first bandpass filter may be smaller or larger than a bandwidth of the second bandpass filter. Preferably, at least one of the first and the second bandpass filter is narrow-banded. That is, at least one of the first and the second band pass filter may comprise a bandwidth of at most 200 nanometer, in particular at most 150 nanometer, preferably at most 100 nanometer.

As regards the use of longpass or shortpass filters, the cut-off wavelength of a longpass filter may be chosen such as to be below the long-wave end of the spectral sensitivity range of the detector, in particular of the respective first or second sensor. Likewise, the cut-off wavelength of a shortpass filter may be chosen such as to be above the short-wave end of the spectral sensitivity range of the detector, in particular of the respective first or second sensor. The cut-off wavelength of the longpass filter and the long-wave end of the spectral sensitivity range of the detector may be selected such as to define a specific wavelength band for restricting the spectrum of the thermal radiation sensed by the detector wavelength. Likewise, the cut-off wavelength of the shortpass filter and the short-wave end of the spectral sensitivity range of the detector may be selected such as to define a specific wavelength band. In other words, the detector in combination with a longpass filter or a shortpass filter may act as bandpass filter. The cut-off wavelength of a longpass filter may be at most 200 nanometer, in particular at most 150 nanometer, preferably at most 100 nanometer below the long-wave end of the spectral sensitivity range of the detector. Likewise, the cut-off wavelength of a shortpass filter may be at most 200 nanometer, in particular at most 150 nanometer, preferably at most 100 nanometer above the short-wave end of the spectral sensitivity range of the detector. When the detector comprises a photodiode, the long-wave end of the spectral sensitivity range is basically determined by the band gap energy of the photosensitive semi-conductor material of the photodiode. Accordingly, the material of the photodiode may be chosen with regard to a long-wave end of its spectral sensitivity range such as to define an upper limit of a wavelength band to be monitored. For example, when an upper limit of the wavelength band to be monitored is about 1.7 micrometer, the detector preferably is or comprises an InGaAs photodiode having a spectral sensitivity range between 0.9 micrometer and 1.7 micrometer.

In case of a detector having at least a first and a second sensor, a first bandpass filter or a first longpass filter or a first shortpass filter may be arranged in front of the first sensor. Alternatively or additionally, a second bandpass filter or a second longpass filter or a second shortpass filter may be arranged in front of the second sensor.

According to one example, the pyrometer may comprise a first and a second bandpass filter arranged in front of a first and second sensor of a detector, respectively. For realizing a dual-wavelength pyrometer, a wavelength band of the first bandpass filter is different from a wavelength band of the second bandpass filter, corresponding to a desired first and second wavelength band. Preferably, at least one of the first and the second band pass filter is narrow-banded.

In alternative to a single-wavelength or a dual-wavelength pyrometer, the pyrometer may be a multi-wavelength pyrometer. A multi-wavelength pyrometer proves advantageous for monitoring the temperature of a target surface having an emissivity which varies with wavelength, in particular non-linearly. Such target surfaces are called non-grey bodies. The multi-wavelength pyrometer is configured to characterize thermal energy and emissivity across the measured wavelengths to accurately determine both, the actual temperature and the emissivity of a non-grey body material. For this, the multi-wavelength pyrometer comprises a detector having more than two sensors, that is, at least three sensors. In general, when the wavelength dependency of the emissivity can be approximated by a function having N unknown parameters, the multi-wavelength pyrometer preferably comprises at least N detectors.

The pyrometer may comprise a detector including at least a first, a second and a third sensor, and preferably also at least a fourth sensor. The first and second sensor may be used for dual-wavelength temperature measurement, that is, used as a dual-wavelength pyrometer as described above. In contrast, the third and the optional fourth sensor may be used to implement additional functionalities, in particular in combination with respective filters in front of the third and the optional fourth sensor. For example, the third and the optional fourth sensor may be used to determine non-grey body emissivity. In particular, the third and the optional fourth sensor may be used to realize a multi-wavelength pyrometer, for example a triple-wavelength pyrometer or a quadruple-wavelength pyrometer. Likewise, the third and the optional fourth sensor may be used to determine a hot spot temperature on the target surface which is different from an average temperature of the target surface determined by the first and second sensors. Moreover, the third and the optional fourth sensor may be used to determine a quantity of vapor or aerosol produced by the aerosol-generating device.

The third and the optional fourth sensor may be of a different sensor type than the first and second sensor. For example, the first and second sensors may be photodetectors, such as photodiodes, whereas the third and the optional fourth sensor may be thermal sensor, for example thermopiles. Likewise, the third and the optional fourth sensor may be of the same sensor type but of different sensitivity. For example, the first and the second sensor may be InGaAs photodiodes, and the third and the optional fourth sensor may be Si photodiodes.

The latter configuration may be advantageously used for detecting hot spots. In such a configuration, the first and second sensors—in combination with respective filters—serve as dual-wavelength pyrometer for measuring an average temperature of the target surface. The third and the optional fourth sensors—without filter—are configured to measure hot spots on the target surface. With regard to the aerosol-generating device according to the invention, hot spots of the target surface are spot-like regions on the target surface whose temperature is above a desired maximum heating temperature, for example, above 350 degree Celsius.

Of course, the third and the fourth sensor may also be identical to the first and second sensor. In this configuration, the detector may be a quadruple-wavelength pyrometer for determining both, the actual temperature and the emissivity of a non-grey body target surface, for example of an aluminum target surface.

Alternatively, the third and the fourth sensor may be combined with a third and fourth bandpass filter, that is, a third bandpass filter is arranged in front the third sensor and a fourth bandpass filter is arranged in front the fourth sensor. The wavelength band of the third bandpass filter is different from a wavelength band of the fourth bandpass filter. Preferably, the wavelength bands of both, the third and the fourth bandpass filter, are narrow-banded, for example, having a bandwidth of at most 200 nanometer, in particular of at most 150 nanometer, preferably of at most 100 nanometer. The wavelength band of the third bandpass filter may be chosen such as to correspond or to cover an absorption peak of a gaseous medium in the line-of sight of the detector. In this configuration, the third and fourth sensor may be used as spectrometer.

For example, water has a pronounced absorption peak around 1.45 micrometer. For detecting how much of the infrared radiation emitted by the target surface is absorbed by water vapor/steam contained in the aerosol in line-of-sight of the pyrometer, the detector may comprise InGaAs photodiodes as a third and fourth sensor and additionally a third bandpass filter in front of the third sensor having a wavelength band at around 1.45 micrometer, and a fourth bandpass filter in front of the fourth sensor having a wavelength band at around 1.45 micrometer. Consequently, this allows estimating the volume of aerosol generated by the aerosol-generating device at a specific temperature. The temperature of the target surface is determined by the first and second sensor serving as dual-wavelength pyrometer.

For dual-wavelength as well as for multi-wavelength pyrometers, the optical system of the pyrometer may comprise at least one beam splitter for splitting, in particular for equally splitting the thermal radiation emitted by the target surface onto the sensors of the pyrometer. Advantageously, the beam splitter is a dichroic beam splitter. A dichroic beam splitter provides two filter bands (one in reflection and one in transmission) without absorption or loss of any impinging light. Alternatively or in addition, the optical system may comprise at least one lens or a lens system for directing and distributing the thermal radiation onto the detectors of the pyrometer.

When using a dual-wavelength and multi-wavelength pyrometer, it is crucial in many applications that the number of photons in each wavelength reaching the respective sensors of the detector of the pyrometer is about the same. Yet, in an aerosol-generating device according to the invention, the aerosol may cause particles and droplets accumulating on a surface of the optical system which is exposed to aerosol volatized from the aerosol-forming substrate upon heating. As a consequence, the number of photons reaching the respective sensors would change and the measurement accuracy could be reduced. To overcome this issue, the optical system may advantageously comprise at least one scattering lens, that is, at least one lens having at least one scattering lens surface. Preferably, the at least one scattering lens surface is far side of the target surface. The scattering surface is a non-smooth lens surface having random irregularities from a smooth lens surface. Due to the scattering surface, the scattering lens scatters thermal radiation emitted by the target surface in all directions. Consequently, the respective sensors of the detector will receive substantially an equal number of photons in all wavelengths, even though a part of a surface of the optical system is blocked by particle or droplet deposits.

In addition to the scattering lens, the optical system may comprise a converging lens for directing the thermal radiation towards the detector. For this, the converging lens is arranged between the scattering lens and the detector.

For the same purpose, the optical system may also comprise at least one Fresnel lens. In particular, the optical system may comprise a Fresnel lens system including at least two Fresnel lenses having their stepped surfaces facing each other. Fresnel lenses prove advantageous due to their thin and light lens design. Preferably, the at least one Fresnel lens is a spherical Fresnel lens.

When using a scattering lens or a Fresnel lens, the optical system preferably is a non-imaging optical system, that is, an optical system that is optimized for optical radiation transfer from a target surface to the detector rather than for image formation. For example, when using a Fresnel lens for a non-imaging system, the lens should be designed to mix up the radiation coming from the target—instead of reproducing an image of it—in order to mitigate adverse effects of dirt accumulating on the lens surface.

To optimize the optical radiative transfer, the optical material of the transparent elements (for example lenses, beam splitters) of the optical system is in particular transparent for wavelength in the near to mid infra-red spectrum. Suitable materials are $CaF_2$ (calcium fluoride), PC (polycarbonate), ABS (acrylonitrile butadiene styrene), PMMA (polymethylmethacrylate) or a COC (cyclic olefin copolymer). These materials comprise a transmissivity of at least 80 percent in the infra-red spectrum up to a wavelength of 1.6 micrometer. In particular, injection molding plastics, such as COC, are preferred as allowing for mass production.

The optical system may comprise a hydrophobic coating at least on a surface being exposed to an aerosol volatized from the aerosol-forming substrate upon heating. The hydrophobic coating advantageously hinders or even prevents dust and aerosol depositing on the coated surface. In addition, the hydrophobic coating facilitates an easy cleaning of the coated surface.

The pyrometer may comprise a casing for enclosing the elements of the pyrometer, in particular for enclosing a detector and an optical system, and possibly also an electrical circuitry of the pyrometer. The casing preferably is opaque or non-transparent, that is lightproof or impervious to light. Thus, the casing provides an optical shielding from ambient light, which advantageously increases the sensitivity and thus the accuracy of the pyrometer. Furthermore, the casing advantageously protects the elements of the pyrometer from aerosol deposits. The casing may comprise an entrance opening allowing thermal radiation to enter the pyrometer. The entrance may be covered by a transparent entrance window which preferably is made of an infra-red transparent material as discussed above. Alternatively, an element of the optical system, in particular a lens, may cover or seal the entrance opening of the casing.

With current technologies, it is possible to build such a pyrometer within a 2×4×4 cubic-millimeter volume, for example using plastic injection molding for the optics fabrication, and flip-chip technology for the detector and the electrical circuitry.

In addition or in alternative to the casing, the aerosol-generating device may comprise a further optical shielding for shielding the pyrometer from ambient light.

As used herein, the term 'aerosol-generating device' is used to describe a device that interacts with an aerosol-forming substrate to generate an aerosol by heating, in particular by electrically heating the substrate. Preferably, the aerosol-generating device is configured to generate an aerosol that is directly inhalable into a user's lungs thorough the user's mouth. Preferably, the aerosol-generating device is a hand-held device, in particular a device resembling the shape of conventional cigarettes.

As used herein, the term 'aerosol-forming substrate' relates to a substrate capable of releasing volatile compounds that can form an aerosol. Such volatile compounds may be released by heating the aerosol-forming substrate. An aerosol-forming substrate may conveniently be part of an aerosol-generating article or smoking article. The aerosol-forming substrate may be a solid or a liquid aerosol-forming substrate. Alternatively, the aerosol-forming substrate may comprise both solid and liquid components. The aerosol-forming substrate may comprise a tobacco-containing material containing volatile tobacco flavor compounds which are released from the substrate upon heating. Alternatively, the aerosol-forming substrate may comprise a non-tobacco material. The aerosol-forming substrate may further comprise an aerosol former that facilitates the formation of a dense and stable aerosol. Examples of suitable aerosol formers are glycerine and propylene glycol.

As used herein, the terms 'aerosol-generating article' refers to an article for interaction with an aerosol-generating device. The article comprises an aerosol-forming substrate. For example, an aerosol-generating article may be a cartridge containing a solid or liquid aerosol-forming substrate. In addition, the article may comprise a heating element which is heatable by the aerosol aerosol-generating device. For example, the heating element may be a susceptor element which is heatable by an induction source of the device when the article is inserted into a housing of the device. In particular, the aerosol-generating article may be a consumable, for example for single use. An article comprising a solid tobacco containing aerosol-forming substrate may be referred to as a tobacco stick.

According to the invention, the pyrometer is configured to determine the temperature of a heated target surface within the device housing. That is, the heated target surface is within the device housing (at least) in use of the device.

Preferably, in use of the device, the heated target surface is in line of sight of the pyrometer. Alternatively, the pyrometer may comprise a fiber-based optical system comprising an optical fiber for collecting and directing the thermal radiation emitted from the target surface to a detector of the pyrometer. Likewise, the device may comprise at least one mirror for directing the thermal radiation emitted from the target surface to a detector of the pyrometer.

The heated target surface may be part of the aerosol-generating device, that is, the aerosol-generating device may comprise the heated target surface. Yet, the heated target surface does not necessarily need to be part of the aerosol-generating device, but may be arranged within the device housing only in use of the device.

Preferably, the heated target surface is a surface area of a heating element used for heating the aerosol-forming substrate. Alternatively, the heated target surface may be in thermal contact with such a heating element.

The heating element may be part of the aerosol-generating device, in particular part of a heater of the aerosol-generating device. In this configuration, the heating element is preferably fixedly arranged within the device housing of the aerosol-generating device. Of course, the heating element may be also detachably arranged or arrangeable within the device housing. That is, the heating element may be configured to be at least partially or even entirely displaceable out of the device housing.

Alternatively, the heater element may be part of an aerosol-generating article including the aerosol-forming substrate to be heated. In this configuration, the heating element is not part of the aerosol-generating device, but rather detachably arrangeable within the device housing. That is, the heating element is insertable and removable from the aerosol-generating device together with the aerosol-forming substrate. In the latter configuration, using a pyrometer proves particularly advantageous due to the non-contact nature of the temperature measurement avoiding the need for thermal contact to the heating element.

The heating element is configured to heat up due to electrically and/or chemically generated thermal energy. Thus, the aerosol-generating device according to the invention may be an electrically and/or chemically heated aerosol-generating device. Accordingly, heat-up of the heating element is caused by resistive heating, induction heating and/or by an exothermal chemical reaction.

In case of the resistive heating, the heating element comprises an electrically conductive material that heats up upon passing an electrical current therethrough. The resistive heating element preferably is part of the aerosol-generating device, in particular part of a resistive heater of the aerosol-generating device. The resistive heater may comprise—in addition to the heating element—an electrical power supply and a controller configured to control the supply of power from the power supply to the heating element.

In case of inductive heating, the heating element preferably is a susceptor element. As used herein, the term 'susceptor element' refers to an element comprising a material that is capable of being inductively heated within an alternating electromagnetic field. This may be the result of at least one of hysteresis losses or eddy currents induced in the susceptor, depending on the electrical and magnetic properties of the susceptor material. Hysteresis losses occur in ferromagnetic or ferrimagnetic susceptors due to magnetic domains within the material being switched under the influence of an alternating electromagnetic field. Eddy currents may be induced if the susceptor is electrically conductive. In case of an electrically conductive ferromagnetic susceptor or an electrically conductive ferrimagnetic susceptor, heat can be generated due to both, eddy currents and hysteresis losses. Accordingly, the susceptor element may comprise a material that is electrically conductive and/or either ferromagnetic or ferrimagnetic. The susceptor element may be part of the aerosol-generating device, in particular part of an inductive heater of the aerosol-generating device. The inductive heater comprises—in addition to the susceptor element—an induction source for generating an alternating electromagnetic field within the device housing such as to induce at least one of heat generating eddy currents or hysteresis losses in the susceptor element. Alternatively, the susceptor element may be part of aerosol-generating article as describe above. In this case, the susceptor element is arranged within the article such as to interact with an alternating electromagnetic field generated by an inductive heater, in particular an induction source, of the aerosol-generating device when the article is received with the housing of the aerosol-generating device. In either configuration, the induction source preferably comprises an induction coil, an electrical power supply and a controller which are operatively connected with each other, wherein the controller is configured to generate an alternating current to be passed through the induction coil.

The heating element may be of any shape or configuration. The heating element may comprise at least one of a rod, a blade, a tape, a strip, a sleeve, a mesh or a wick, or may be of particulate configuration. For example, the heating element may comprise a heating blade or heating rod configured for penetrating an aerosol-forming substrate upon inserting the substrate into the device housing. Likewise, the heating element may form at least a portion of a receiving cavity within the device housing for receiving the aerosol-forming substrate to be heated. The heating element may also form at least a portion of an aerosol-generating article, for example a cartridge, which includes the aerosol-forming substrate and is configured to be received within the housing of the aerosol-generating device. Alternatively, in particular when being part of an aerosol-generating article, the heating element may comprise a heating blade, a heating strip, a heating rod, a heating tape or a heating sleeve being arranged in close proximity to aerosol-forming substrate included in an aerosol-generating article. The heating element may be a heating mesh or a heating wick, either as part of the aerosol-generating device or as part of an aerosol-generating article. The mesh or wick configuration is particularly suitable for use with liquid aerosol-forming substrates.

According to the invention there is also provided an aerosol-generating system comprising an aerosol-generating device according to the invention and as described above. The system further comprises an aerosol-generating article for use with the device which comprises the aerosol-forming substrate to be heated. In particular, the device housing is configured to at least partially receive the article.

According to a particular aspect of the invention, the device comprises a heater which is configured for generating heat in a heating element. The heating element is arranged or arrangeable within the aerosol-forming substrate of the article and comprises the heated target surface whose temperature is monitored by the pyrometer of the device. As described above with regard to the aerosol-generating device, the heating element and thus the heated target surface may be either part of the device or of the article.

Further features and advantages of the aerosol-generating system according to the invention have been described with regard to the aerosol-generating device and article and will not be repeated.

The invention will be further described, by way of example only, with reference to the accompanying drawings, in which.

Figure 1:
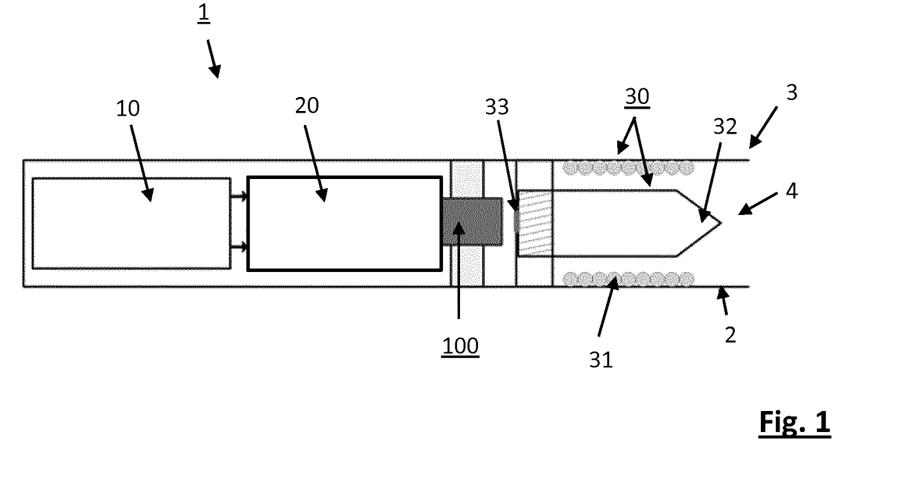
FIG. 1 shows a schematic illustration of an aerosol-generating device according to a first embodiment of the invention.

FIG. 1 schematically illustrates a first embodiment of an aerosol-generating device 1 according to the present invention. The device 1 is configured for generating an inhalable aerosol by inductively heating a solid aerosol-forming substrate. For this, the substrate may be replaceably arranged in a receiving cavity 4 formed at the proximal end 3 of the elongate housing 2 of the device 1. The substrate may be part of an aerosol-generating article (not shown) that is configured to be at least partially received in the receiving cavity 4. In the present embodiment, the device 1 comprises an inductive heater 30 for heating the substrate. The inductive heater 30 comprises a helical induction coil 31 surrounding the receiving cavity 4 for generating an alternating electromagnetic field within the receiving cavity 4. The heater 30 further comprises a susceptive heating element 32. In the present embodiment, the heating element 32 is a tapered susceptor blade 32 made of stainless steel which is arranged within the receiving cavity 4 and configured to penetrate the aerosol-forming substrate upon inserting the aerosol-generating article into the receiving cavity 4. When passing an alternating driving current through the induction coil 31, the alternating electromagnetic field induces hysteresis losses and/or eddy currents in the susceptor blade 32 depending on its electrical and magnetic material properties. As a consequence, the heating element 32 heats up which in turn heats the aerosol-forming substrate when being in thermal contact with the susceptor blade 32. For replacement and cleaning purposes, the susceptor blade 32 may be detachably arranged at a distal end of the receiving cavity 4. Alternatively, the susceptor blade may be part of an aerosol-generating article to be inserted into the receiving cavity 4 of the device 1.

Of course, the device according to FIG. 1 may be also configured for resistive heating. For example, instead of a susceptor blade, the device 1 may comprise a resistive or restively heated heater blade.

The device 1 further comprises an electrical circuitry 20—powered by a battery 10—which is configured, inter alia, for generating the alternating driving current. The electrical circuitry 20 comprises a controller (not shown) for controlling the heating process.

Controlling the heating temperature requires temperature monitoring of the heating element 32. For this, the device 1 according to FIG. 1 comprises a dual-wavelength pyrometer 100 for measuring the absolute temperature of a target surface 33 on the heating element 32. In the present embodiment, the target surface 33 is a portion of the rear surface of the susceptor blade 32 which is in direct line-of-sight of the pyrometer 100.

As can be further seen from FIG. 1, the pyrometer 100 is operatively connected with the electrical circuitry 20 of the device. In the present embodiment, the electrical circuitry 20 is also configured to evaluate the output signal of the pyrometer 100 in order to determine the absolute temperature of a target surface 33. The electrical circuitry may comprise at least one of a transimpedance amplifier for current-to-voltage conversion, an inverting signal amplifier, a single-ended to-differential converter, an analog-digital converter and a micro-controller.

Further details of the dual-wavelength pyrometer 100 are described below with regard to the embodiments shown in FIGS. 4 and 5.

Figure 2:
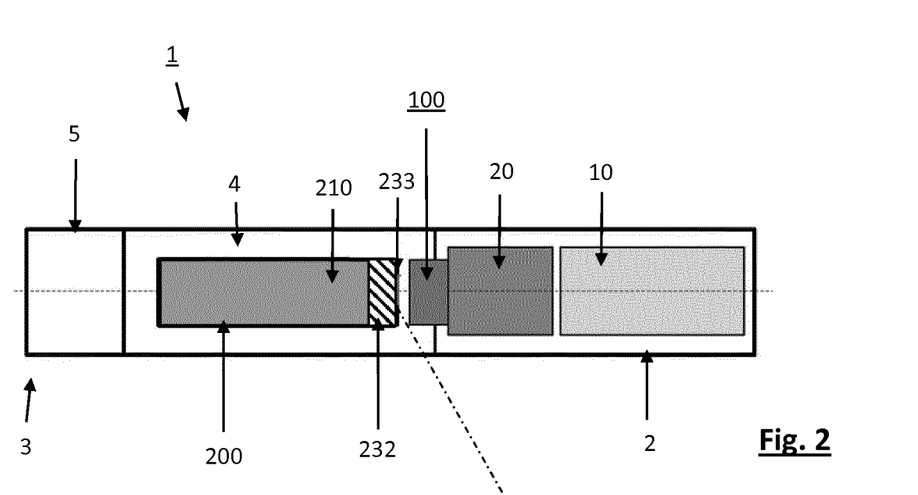
FIG. 2 shows a schematic illustration of an aerosol-generating device according to a second embodiment of the invention in combination with an aerosol-generating article.

FIG. 2 schematically illustrates a second embodiment of an aerosol-generating device 1 according to the present invention. Like the device according to FIG. 1, the device according to FIG. 2 is configured for inductive heating. Therefore, similar or identical features are denoted with identical reference numbers. In contrast to the embodiment shown in FIG. 1, the susceptive heating element 232 is not part of the device 1 but part of an aerosol-generating article 200 which includes a liquid aerosol-forming substrate 210 to be heated. In the present embodiment, the susceptive heating element 232 is a mesh susceptor 232 made of stainless steel which is arranged at a distal end of the cartridge-like article 200. When the article 200 is placed in the receiving cavity 4 formed within the device housing 2, the mesh susceptor 232 may experience an alternating electromagnetic field generated by an induction source of the device (not shown) which causes the susceptive material of the mesh to heat up. The mesh susceptor 232 is configured such that the liquid aerosol-forming substrate forms a meniscus in the interstices of the mesh susceptor 232. When the mesh susceptor 232 is heated, liquid aerosol-forming substrate is continuously vaporized from the mesh susceptor 23 into the receiving cavity 4. There, the aerosol is formed by the vaporized substrate and withdrawn into an airflow passage extending through the cavity 4 towards a mouthpiece 5 at a proximal end 3 of the device 1.

Of course, the device according to FIG. 2 may be alternatively configured for resistive heating, for example, by using a restively heated mesh or resistive mesh which may be either part of the device 1 or the article 200.

Figure 3:
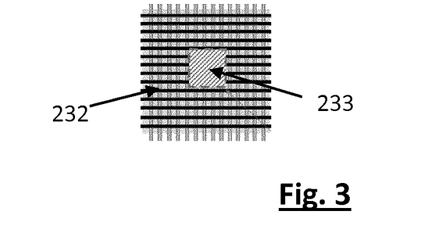
FIG. 3 shows a detail view of the aerosol-generating article used with the aerosol-generating device according to FIG. 2.

For measuring the absolute temperature of the mesh-susceptor 232, the device 1 according to FIG. 2 also comprises a dual-wavelength pyrometer 100. The pyrometer is arranged at a distal end of the receiving cavity 4 such as to directly face the mesh susceptor 232 when the aerosol-generating article 200 is placed in the device housing 2. As can be seen in FIG. 3, the pyrometer monitors only a portion 233 of the front surface of the mesh susceptor 232 which is in direct line-of-sight of the pyrometer 100. The target surface 233 measures about 1 millimeter times 1 millimeter.

In both embodiments according to FIGS. 1 and 2, the pyrometer is over-molded in a plastic part used to completely isolate the receiving cavity 4 from a rear cavity within the device housing 2 where the electrical circuitry 20 and the battery 10 are arranged. With this arrangement the pyrometer 100 can be kept in a fixed line-of-sight opposite to the target surface 33, 233 whose temperature is to be measured. With regard to the embodiment according to FIG. 2, this solution also allows to host the expensive pyrometer 100 with the durable device 1, while leaving the cheap mesh susceptor 232 with the article for improved hygiene. Even more important with regard to FIG. 2, the pyrometer 100 allows for contactless temperature measurement, thus avoiding the need for thermal contact to the heating element. The need for thermal contact would be technically impractical as the heating element is part of the article and thus removable from the device.

Figure 4:
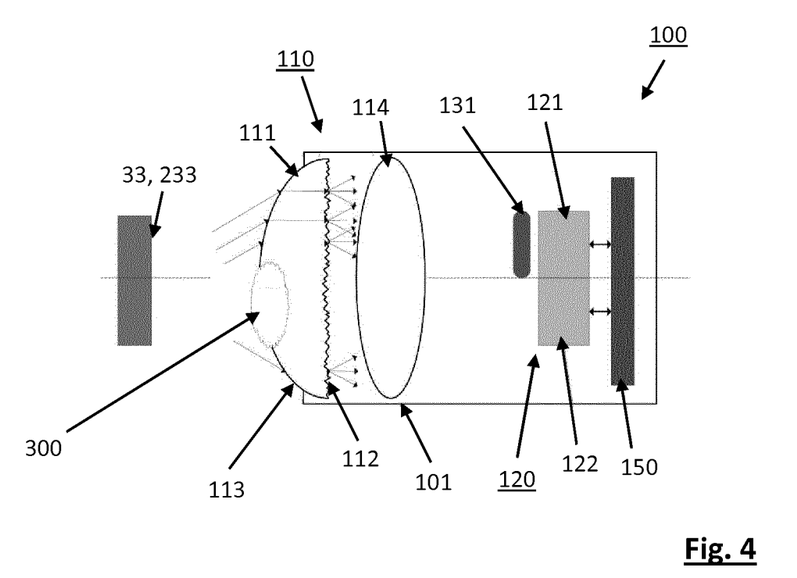
FIG. 4 shows a schematic illustration of a pyrometer according to a first embodiment of the invention.

FIG. 4 schematically illustrates a first embodiment of a dual-wavelength pyrometer 100 which can be used in the aerosol-forming devices 1 according to FIG. 1 and FIG. 2 for determining a temperature of the respective target surface 33, 233. In the present embodiment, the dual-wavelength pyrometer 100 comprises a photodetector 120 which includes a first and a second InGaAs photodiode 121, 122 arranged side by side. InGaAs photodiodes are preferred as having a faster response time, higher quantum efficiency and lower dark current for the same sensor area as compared to other materials, such as Ge.

Dual-wavelength pyrometry requires measuring the thermal radiation emitted by the target surface at two wavelength or wavelength bands. In the present embodiment, this is accomplished by using a longpass filter 131 arranged in front of the first sensor 121 only. The longpass filter 131 has a cut-off wavelength of 1.6 micrometer. InGaAs is sensitive for wavelengths between 0.9 micrometer and 1.7 micrometer. Thus, the cut-off wavelength of the longpass filter 131 and the long-wave end of the spectral sensitivity range of the InGaAs sensor 121 provide an effective bandpass filtering of the thermal radiation sensed by the first sensor 121 to the range of 1.6 micrometer to 1.7 micrometer. In contrast, the second sensor 122 has no filter in front and thus monitors the full spectral band according to the sensitivity of InGaAs in the range of 0.9 micrometer to 1.7 micrometer. Hence, due to the cut-off wavelength of the longpass filter 131, a difference between the output signals of the first and second sensor 121, 122 is achieved which is reasonably measurable and thus well suited for determining the temperature of the heated target surface 33, 233 as described above.

As further described above, at least the second sensor 122 needs to be manually calibrated across the full wavelength spectrum. This can be done for example by using a blackbody emitter at different known temperatures of the black body. The first sensor 121 may be also calibrated in the same way. In principle, once the initial calibration is made, the emissivity of the target surface 33, 233 does not need to be known any longer (in case the target surface 33, 233 is a grey body). In the case that the target surface is a non-grey body, a second calibration should be made taking into account the variation of emissivity. This calibration needs to be done only for one device of a specific type.

Advantageously, the dual-wavelength pyrometer 100 is inherently accurate as it allows not only for compensating for emissivity variations, but also for partially filled fields of view and optical obstructions between the target surface and the detector of the pyrometer.

For collecting thermal radiation emitted from the heated target surface 33, 233 and for directing the thermal radiation towards the detector 120, the dual-wavelength pyrometer 100 comprises an optical system 110. In the present embodiment, the optical system 100 comprises two lenses, a converging lens 114 and a semi-convex lens 111. The optical system 100 provides a field of view on the target surface 33, 233 having a diameter of at least 1 millimeter.

In use of the aerosol-generating device 1, aerosol particles and droplets 300 may accumulate on the front surface of the optical system 120 which is exposed to the aerosol within the receiving cavity 4. As a consequence, the number of photons at each wavelength reaching the first and second sensor 121, 122 could change, which in turn could reduce the measurement accuracy. To overcome this issue, lens 111 is configured as scattering lens having a scattering back lens surface 112. The scattering surface 112 is a non-smooth lens surface having random irregularities from a smooth lens surface. Due to the scattering surface 112, the scattering lens 111 scatters thermal radiation emitted by the target surface 33, 233 in all directions. Consequently, the first and second sensors 121, 122 receive substantially an equal number of photons in all wavelengths, even though a part of a surface of the optical system is blocked by particle or droplet deposits 300.

Figure 5:
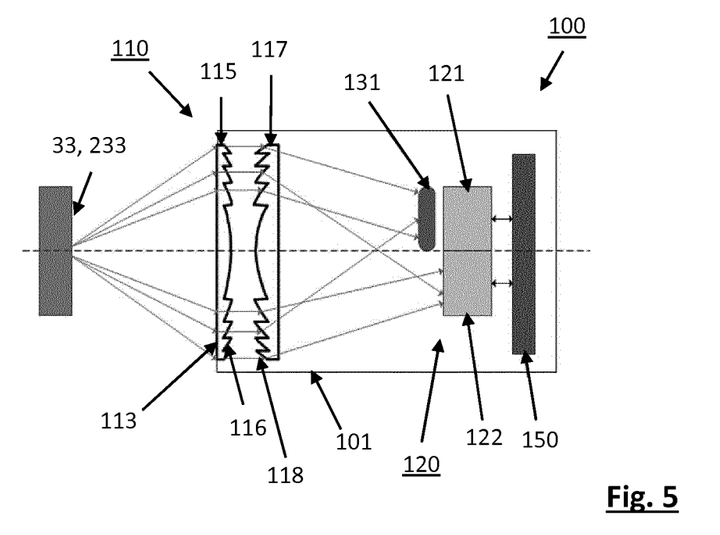
FIG. 5 shows a schematic illustration of a pyrometer according to a second embodiment of the invention.

FIG. 5 schematically illustrates an alternative embodiment of the optical system 120. For the same purpose, the optical system 120 comprises a Fresnel lens system including two Fresnel lenses 115, 117 having their stepped surfaces 116, 118 facing each other. Fresnel lenses prove advantageous due to their thin and light lens design. Both Fresnel lenses 115, 117 are spherical Fresnel lenses.

In both embodiments according to FIGS. 4 and 5, the optical system 120 is a non-imaging optical system optimized for radiation transfer from the target surface 33, 233 to the sensors 121 and 122.

To further optimize the optical radiative transfer, the optical material of the lenses, 111, 114, 115, 117 is transparent for wavelength in the infra-red spectrum. In both embodiments, injection molding plastics, such as COC, is used as lens material allowing for mass production.

As can be further seen from FIGS. 4 and 5, the pyrometer 100 comprises a casing 101 for enclosing the sensors 121, 122 and the optical system 120. The casing may also enclose an electrical circuitry 150 of the pyrometer 100. The casing 101 is non-transparent and thus provides an optical shielding from ambient light, which advantageously increases the sensitivity and thus the accuracy of the pyrometer 100. Furthermore, the casing 101 advantageously protects the elements of the pyrometer 100 from aerosol deposits. In both embodiments according to FIGS. 4 and 5, the front lens 11, 115 seals the entrance opening of the casing 101.

In order to hinder or even prevent dust and aerosol deposits on the front lenses 111, 115, the front surfaces of these lenses comprise a hydrophobic coating 113. The hydrophobic coating 113 also facilitates an easy cleaning of the front lens 111, 115.

The invention claimed is:

1. An aerosol-generating device configured for generating an aerosol by heating an aerosol-forming substrate, the device comprising a device housing for receiving the aerosol-forming substrate, and a pyrometer for determining a temperature of a heated target surface within the device housing, wherein the pyrometer is a dual-wavelength pyrometer or a multiple-wavelength pyrometer that is configured to measure thermal radiation at least at a first wavelength band and a second wavelength band, wherein the second wavelength band is broader than the first wavelength band, and wherein the pyrometer includes a detector comprising at least a first and a second sensor, wherein the first and the second sensor are arranged adjacent to each other side by side, and wherein the pyrometer comprises an optical system for collecting thermal radiation emitted from the heated target surface, wherein the optical system comprises a lens having a lens surface far side of the target surface which is a scattering surface.

2. The device according to claim 1, further comprising an optical shielding for shielding the pyrometer from ambient light.

3. The device according to claim 1, wherein a first optical bandpass or longpass or shortpass filter is arranged in front of the first sensor.

4. The device according to claim 1, wherein a second optical bandpass or longpass or shortpass filter is arranged in front of the second sensor.

5. The device according to claim 1, wherein the detector comprises at least a third sensor.

6. The device according to claim 5, wherein a spectral sensitivity of the third sensor is different from a spectral sensitivity of the first and second sensor.

7. The device according to claim 5, wherein the detector comprises at least a fourth sensor.

8. The device according to claim 7, wherein a spectral sensitivity of the fourth sensor is different from a spectral sensitivity of the first and second sensor.

9. The device according to claim 7, wherein a third optical bandpass filter is arranged in front of the third sensor and a fourth optical bandpass filter is arranged in front of the fourth sensor, and wherein a wavelength band of the third bandpass filter is different from a wavelength band of the fourth bandpass filter.

10. An aerosol-generating system comprising an aerosol-generating device according to claim 1 and an aerosol-generating article for use with the device comprising an aerosol-forming substrate.

11. The system according to claim 10, wherein the device comprises a heater for generating heat in a heating element that is arranged or arrangeable within the aerosol-forming substrate of the article, and wherein the heating element comprises the heated target surface.

* * * * *

UNITED STATES PATENT AND TRADEMARK OFFICE
CERTIFICATE OF CORRECTION

| | |
|---|---|
| PATENT NO. | : 11,644,365 B2 |
| APPLICATION NO. | : 16/650914 |
| DATED | : May 9, 2023 |
| INVENTOR(S) | : Michel Bessant et al. |

Page 1 of 1

It is certified that error appears in the above-identified patent and that said Letters Patent is hereby corrected as shown below:

On the Title Page

Item (72) Inventor: Riccardo Riva Reggiori, St. Sulpice (IT) should be "Riccardo Riva Reggiori, St. Sulpice (CH)"

Signed and Sealed this
Twentieth Day of June, 2023

Katherine Kelly Vidal
*Director of the United States Patent and Trademark Office*